United States Patent [19]

Phillipps et al.

[11] Patent Number: 4,497,805
[45] Date of Patent: * Feb. 5, 1985

[54] 11α-AMINO-ANDROSTANES

[75] Inventors: Gordon H. Phillipps, Wembley; David C. Humber, Ealing; George B. Ewan, Northolt; Barry A. Coomber, Pinner; Anthony J. Pateman, Uxbridge, all of England

[73] Assignee: Glaxo Group Limited, London, England

[*] Notice: The portion of the term of this patent subsequent to Oct. 12, 1999 has been disclaimed.

[21] Appl. No.: 475,899

[22] Filed: Mar. 16, 1983

Related U.S. Application Data

[63] Continuation of Ser. No. 383,210, May 28, 1982, abandoned.

[30] Foreign Application Priority Data

May 29, 1981 [GB] United Kingdom ................ 8116410

[51] Int. Cl.³ .......................... A01N 45/00; C07J 3/00
[52] U.S. Cl. .................................. 514/172; 260/397.1; 514/176; 514/182
[58] Field of Search ...................... 260/397.1; /Machine Searched Steroids

[56] References Cited

U.S. PATENT DOCUMENTS 4,353,898 10/1982 Phillipps et al. ................ 260/397.1

Primary Examiner—Elbert L. Roberts
Attorney, Agent, or Firm—Bacon & Thomas

[57] ABSTRACT

Compounds of the formula

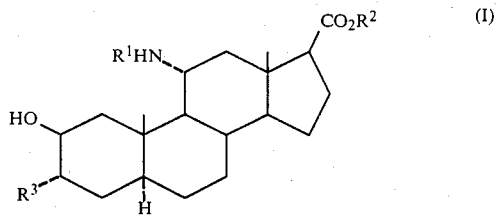

wherein $R^1$ is a $C_{1-8}$ alkyl group or a $C_{3-7}$ cycloalkyl group;

$R^2$ is a $C_{1-6}$ alkyl group or a $C_{3-7}$ cycloalkyl group;

$R^3$ is a hydroxy group or a group of formula $-OR^4$ or $-OCOR^5$ where $R^4$ is an alkyl or alkenyl group which may contain up to 6 carbon atoms (or such a group substituted by halogen, $C_{1-6}$ alkoxy, carboxyl, phenyl, phenyl substituted by nitro, halo, $C_{1-4}$ alkoxy or $C_{1-4}$ alkyl), a $C_{3-7}$ cycloalkyl group, a phenyl group (or such a group substituted by nitro, halo, $C_{1-4}$ alkoxy or $C_{1-4}$ alkyl), or a carbon-attached 5-7 membered heterocyclic ring in which the hetero atom is selected from nitrogen, oxygen and sulphur, and $R^5$ is a hydrogen atom or a group $R^4$ as defined above;

and the D-homo analogues thereof having the group $-CO_2R^2$ (wherein $R^2$ is as defined above) at the 17aβ-position, and salts thereof have activity as antidysrhythmic agents and may be applicable for the treatment of dysrhthmias in humans or animals. The compounds may be provided in the form of compositions in admixture with pharmaceutical carriers or excipients and may be prepared by a variety of processes known for producing steroids of this type. The invention also provides intermediates for the preparation of compounds of formula (I), in which intermediates $R^1$ and/or $R^2$ is replaced by a hydrogen atom, and processes for the preparation of such intermediates.

18 Claims, No Drawings

11α-AMINO-ANDROSTANES

This application is a continuation of application Ser. No. 383,210, filed May 28, 1982, now abandoned.

This invention relates to aminosteroids having antidysrhythmic activity, and in particular to certain compounds in the androstane series having a substituted amino group at the 11α-position and a hydroxy group in the 2β-position.

The aim of antidysrhythmic therapy is to return hazardous abnormal heart rhythms towards normal, or to reduce the likelihood of hazardous rhythms developing in patients at risk as a result of hypertension, atheromas, diabetes or heart conditions such as myocardial disease, ischaemia or infarction.

It is recognised that dysrhythmias in patients with heart attack and other conditions are treatable and preventable. There are several drugs available for the treatment of ventricular dysrhythmias but their application is limited by their lack of efficacy or by their toxicity which gives rise to various side effects.

Thus there is a demand for drugs suitable for use in the treatment of patients with dysrhythmias, and therefore in danger of sudden cardiac death. Furthermore, there is a demand for such drugs for administration, for example for long term prophylaxis, to patients at risk of developing dysrhythmias, in which case, activity on oral administration is desirable.

In Belgian Patent Specification 853227 there is described a group of 11α-tertiary amino-3α-hydroxy steroids having anaesthetic activity. In addition to the 11α-tertiary amino and 3α-hydroxy groups, the possibility of the compounds possessing various substituents in other positions including the 17β-position is allowed for, one possible 17β-substituent being a $C_{1-5}$ alkoxycarbonyl group. Corresponding 11α-primary and secondary amino steroids are also described as intermediates for the preparation of the tertiary amino compounds. There is no specific disclosure in Belgian Pat. No. 853227 of any 11α-primary or secondary amino-17β-alkoxycarbonyl compounds and no anaesthetic activity is ascribed to any such compounds specifically. Moreover, there is no disclosure whatsoever in Belgian Pat. No. 853227 of any 2β-hydroxy-11α-primary or secondary amino compounds. Furthermore, no antidysrhythmic activity has been ascribed to any of the compounds in the above Belgian Patent Specification, or indeed to any compounds of comparable structure.

We have now discovered that a group of steroids having a primary or secondary amino group at the 11α-position and a 2β-hydroxy group have promising antidysrhythmic activity.

Accordingly the invention provides 11α-amino-2β-hydroxy-androstanes of the formula

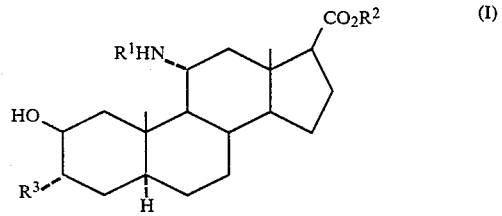

wherein $R^1$ is a $C_{1-8}$ alkyl group or a $C_{3-7}$ cycloalkyl group;

$R^2$ is a $C_{1-6}$ alkyl or a $C_{3-7}$ cycloalkyl group; and $R^3$ is a hydroxy group or a group of formula $-OR^4$ or $-OCOR^5$ where $R^4$ is an alkyl or alkenyl group which may contain up to 6 carbon atoms (or such a group substituted by halogen, $C_{1-6}$ alkoxy (e.g. methoxy or ethoxy), carboxy, phenyl, phenyl substituted by nitro, halo, $C_{1-4}$ alkoxy (e.g. methoxy) or $C_{1-4}$ alkyl (e.g. methyl)), a $C_{3-7}$ cycloalkyl group, a phenyl group (or such a group substituted by nitro, halo, $C_{1-4}$ alkoxy (e.g. methoxy) or $C_{1-4}$ alkyl (e.g. methyl)), or a carbon-attached 5-7 membered heterocyclic ring in which the heteroatom is selected from nitrogen, oxygen and sulphur, and $R^5$ is a hydrogen atom or a group $R^4$ as defined above; and the D-homo analogues thereof having the group $-CO_2R^2$ (wherein $R^2$ is as defined above) at the 17aβ-position, and salts thereof.

The compounds of the invention have been found to possess useful antidysrhythmic activity in the tests which have been carried out, and have potential as antidysrhythmic drugs.

Where either of the groups $R^1$ and $R^2$ is an alkyl group it may be straight or branched-chain group.

Where $R^1$ is a cycloalkyl group, it may be, for example, a cyclobutyl, cyclopentyl, cyclohexyl or cycloheptyl group.

Where $R^1$ is an alkyl group it preferably has 3-7 carbon atoms, and may, for example, be a propyl, butyl, pentyl, isopentyl, hexyl, isohexyl or neohexyl group.

Where $R^2$ is a cycloalkyl group it may be, for example, a cyclopropyl, cyclobutyl, cyclopentyl or cyclohexyl group. Where $R^2$ is an alkyl group, it may be, for example, a methyl, ethyl, propyl, isopropyl, butyl or isopentyl group. $R^2$ is preferably a $C_{1-3}$ alkyl group.

Where $R^4$ or $R^5$ is an alkyl or alkenyl group, it may, for example, be a methyl, ethyl, propyl or propenyl group. Where $R^4$ or $R^5$ is substituted there will generally be one such substituent except in the case of hydrogen substituents where there may be, for example, 1-3 substituents. Examples of suitable halogen substituents are fluoro, chloro and bromo.

Where $R^4$ or $R^5$ is a carbon-attached heterocyclic group it may be saturated or unsaturated, containing up to 3 double bonds. Examples of such groups include tetrahydropyranyl, tetrahydrofuranyl, furyl, thienyl and pyridyl.

Where compounds having good activity following oral administration are desired, $R^2$ is preferably a methyl or ethyl group.

Particularly preferred compounds are those in which $R^1$ is an isopentyl, hexyl, isohexyl, neohexyl, cyclopentyl or cyclohexyl group; $R^2$ is a methyl or ethyl group, especially a methyl group; and $R^3$ is a hydroxy group.

Ring D conveniently has 5 members.

The compounds of formula (I) and D-homo analogues thereof may form acid addition salts; physiologically acceptable acid addition salts are preferred. Those compounds in which the group $R^3$ contains a carboxy group may also form salts with bases or exist in zwitterionic forms. The term "salts" is used herein, unless otherwise indicated to designate acid addition salts, base salts and zwitterionic forms.

Examples of acid addition salts are hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates. The hydrochlorides are preferred acid addition salts.

The salts with bases may be salts with inorganic bases such as alkali metal salts, e.g. sodium, potassium and lithium salts; alkaline earth metal salts, e.g. calcium and magnesium salts; and ammonium salts, or salts with organic bases, e.g. amine salts.

Individual compounds which are preferred on the basis of their high antidysrhythmic activity include:
1. Methyl 2β,3α-dihydroxy-11α-(3-methylbutylamino)-5α-androstane-17β-carboxylate;
2. Methyl 11α-cyclohexylamino-2β,3α-dihydroxy 5α-androstane-17β-carboxylate;
3. Methyl 3α-ethoxy-2β-hydroxy-11α-(3-methylbutylamino)-5α-androstane-17β-carboxylate; and
4. Methyl 3α-acetoxy-2β-hydroxy-11α-(3-methylbutylamino)-5α-androstane-17β-carboxylate;
and their physiologically acceptable acid addition salts, e.g. their hydrochlorides.

Compound 1 above and its physiologically acceptable acid addition salts, such as the hydrochloride salt, are highly preferred. Investigations both in vitro and in experimental animals have shown that this compound possesses a highly desirable combination of pharmacological properties. In particular, against aconitine-induced dysrhythmias in anaesthetised rats the compound exhibited high levels of activity following both oral and intravenous administration. A single oral dose of the compound gave a prolonged duration of action. The compound was effective, when administered intravenously or orally, against post-infarction dysrhythmias in the conscious dog.

The invention further provides compounds of formula (I), D-homo analogues thereof and their physiologically acceptable salts for use in a method of treatment of the human or animal, in particular mammalian, body to combat cardiac dysrhythmias therein. The invention also provides compounds of formula (I), D-homo analogues thereof and physiologically acceptable salts thereof in association with instructions for their use as antidysrhythmic agents.

The compounds may be used in the treatment of patients with disturbances of cardiac rhythm, whether arising spontaneously, or as a result of treatment with other drugs, e.g. cardiac glycosides, or as a consequence of myocardial ischaemia or infarction. Alternatively they may be used for the prophylactic treatment of patients at risk of cardiac rhythm disturbances or sudden coronary death.

Accordingly, the invention provides a method of therapy or prophylaxis of a human or animal, in particular mammalian, body suffering from or liable to cardiac dysrhythmias which method comprises administering to the said body an effective amount of a compound of formula (I), a D-homo analogue thereof or a physiologically acceptable salt thereof.

As a further aspect of the invention there are provided compounds of the formula

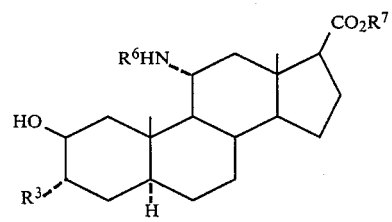

(wherein $R^6$ is a hydrogen atom, a $C_{1-8}$ alkyl group or a $C_{3-7}$ cycloalkyl group; $R^7$ is a hydrogen atom, a $C_{1-6}$ alkyl group or a $C_{3-7}$ cycloalkyl group; and $R^3$ is as hereinbefore defined; with the proviso that at least one of $R^6$ and $R^7$ is a hydrogen atom) and the D-homo analogues thereof having the group $CO_2R^7$ (wherein $R^7$ is as defined above) at the 17aβ-position, and salts thereof.

The compounds of formula (II) and the D-homo analogues thereof may form acid addition salts. Those compounds in which the group —$CO_2R^7$ represents a carboxyl group may also form salts with bases or exist as zwitterions.

Examples of salts are those give above in connection with the compounds of formula (I).

Compounds of formula (II) and the D-homo analogues thereof are useful as intermediates in the preparation of compounds of formula (I) or the D-homo analogues thereof using the methods described hereinafter.

The compounds of the invention may be prepared by a number of different methods, using generally known techniques. Suitable methods are described below:
1. A substituent on the 11α-amino function may be introduced by alkylating or cycloalkylating the corresponding 11α-amino compound of formula II in which $R^6$ is hydrogen. This alkylation (or cycloalkylation) may suitably be effected by reductive alkylation (or cycloalkylation) with an appropriate monocarbonyl compound in the presence of a reducing agent or by reaction with a compound of the formula $R^1X$ wherein $R^1$ is other than hydrogen and X is a readily displaceable atom or group such as halide (e.g. iodide), a hydrocarbylsulphonyloxy group (e.g. toluene-p-sulphonyloxy), a hydrocarbyloxysulphonyloxy group (e.g. methoxysulphonyloxy) or a dialkoxyphosphonyloxy group (e.g. dimethoxyphosphonyloxy).

When carried out on compounds of formula (II) in which $R^7$ is also hydrogen, such reaction with $R^1X$ may result in esterification to form a compound in which $R^1 = R^2$. The group $R^2$ may, if not desired in the final product, subsequently be replaced by transesterification in one or more stages, for example as set out under 4 below. However, where $R^7$ is hydrogen and the initial product is a carboxylic acid, this should be esterified, for example as set out under 4 below. The introduction of the substituent on the 11α-amino function by reaction with $R^1X$ is preferably carried out in the presence of a base (e.g. potassium carbonate or silver oxide) in solution at any suitable temperature from ambient to reflux (e.g. +20° to +100° C.). The reaction is conveniently effected in a suitable reaction solvent. Suitable solvents include ethers (e.g. dioxan), substituted amides (e.g. N,N-dimethylformamide or N,N-dimethylacetamide), sulphoxides (e.g. dimethylsulphoxide), alkanols (e.g. ethanol or methanol) or acetonitrile.

When X is a chlorine or bromine atom, the reaction may be facilitated by addition of an iodide such as sodium iodide.

The reducing agents which may be used in reductive alkylation or cycloalkylation are those generally known for the reduction of imines, examples being formic acid (e.g. at any suitable temperature up to 100°-120° C., for example from ambient temperature up to 100° C., and using the carbonyl compound as the reaction solvent, in the presence or absence of water), an alkali metal borohydride or cyanoborohydride (e.g. sodium borohydride or cyanoborohydride, using an alcohol such as ethanol as solvent, suitably at room temperature), iron pentacarbonyl or an alkali metal hydrogen iron carbonylate (e.g. $Fe(CO)_5$ or $MHFe(CO)_4$ where M is sodium or potassium, at any suitable temperature up to reflux using an ether such as tetrahydrofuran or an alcohol or aqueous alcohol as solvent), hydrogen in the presence of a metal catalyst (using an alcohol, e.g. ethanol, an ether, e.g. dioxan or an ester, e.g. ethyl acetate, as reaction solvent, conveniently at ambient temperature), or aluminium amalgam in the presence of water (conveniently at ambient temperature, and in the presence of an ether solvent such as tetrahydrofuran).

The metal catalyst may, for example, be a noble metal catalyst such as platinum, platinum oxide, palladium or rhodium. The catalyst may be supported, e.g. on charcoal or kieselguhr. A homogeneous catalyst such as tristriphenylphosphine rhodium chloride may also be used. If desired the intermediate imino compound may be isolated. Thus, for example, the use of formaldehyde, acetaldehyde, 3-methylbutanal or cyclohexanone can provide the $11\alpha$-N-methyl, N-ethyl, N-iso-pentyl or N-cyclohexyl amines respectively.

It will be appreciated that the conditions for reductive alkylation or cycloalkylation should be chosen to give predominantly the desired N-monosubstituted compound, and minimise production of the corresponding N,N-disubstituted compound. Reductive alkylation or cycloalkylation of the compounds of formula (II) in which $R^7$ is a hydrogen atom is preferably effected under basic conditions. Where $R^7$ is hydrogen the initial product will be a carboxylic acid which should then be esterified to form an ester of formula (I), for example as set out in 4 below.

Compounds of formula (II) in which $R^6$ is hydrogen may be prepared by reduction of the corresponding 11-oxime. Such a reduction may be effected with an alkali or alkaline earth metal in an alcohol and/or an amine and/or ammonia, e.g. sodium in n-propanol, if desired in the presence of a suitable solvent, e.g. tetrahydrofuran, at any suitable temperature up to and preferably at reflux.

The 11-oximes may themselves be prepared from the corresponding 11-oxo compounds. The 11-oxo compound may for example be reacted with hydroxylamine under strongly alkaline conditions in aqueous alcohol (e.g. ethanol), preferably at reflux. The reaction may also be carried out under acidic conditions (ca. pH 4), e.g. in buffered pyridine.

The severe conditions used in the reduction of the 11-oxime make it necessary or desirable that certain substituents for example the $17\beta$-alkoxycarbonyl substituent and the $3\alpha$-alkanoyloxy substituent should be introduced after the formation of the $11\alpha$-amino group.

2. Opening of a corresponding 2,3-epoxide.

$2\beta,3\alpha$-Dihydroxy compounds may be prepared by treating the corresponding $2\alpha,3\alpha$-epoxide with water under acidic conditions (for example in the presence of sulphuric acid or perchloric acid) or a compound which produces the anion $OH^-$ and then (when the initial product possesses a deprotonated $3\alpha$-hydroxy group) treating the product with a source of protons (e.g. aqueous ammonium chloride) to form the $3\alpha$-hydroxy group. Examples of reagents which produce $OH^-$ anions are alkali metal or ammonium hydroxides. The reaction may be carried out at any suitable temperature up to reflux, and in a suitable solvent medium (e.g. a hydrocarbon, halogenated hydrocarbon or ether).

The use of a compound which produces the anion $OH^-$ may result in deesterification of a $17\beta$-carboxylic ester group if present to give a compound of formula (II) in which $R^7$ is hydrogen. A desired ester group may be introduced using the procedure set out under 4 below.

The starting materials required for the opening of a $2\alpha,3\alpha$-epoxide may for example be prepared by first introducing the desired $11\alpha$-amino group (e.g. by the method of reaction 1 above) using a $\Delta^2$-starting material, then forming a salt (e.g. with toluene-p-sulphonic acid) and then epoxidising the $\Delta^2$-compound with a peracid, finally regenerating the free base. $\Delta^2$-Compounds may be prepared by formation of the 3-methanesulphonate and subsequent elimination of methanesulphonic acid.

When the epoxidation is effected in the presence of a primary $11\alpha$-amino group the amino group may also be protected for example as a trichloroethoxycarbonyl derivative. The trichloroethoxycarbonyl group can be removed subsequently by hydrolysis with alkali or preferably by reduction with zinc and acetic acid.

$2\beta,3\alpha$-dihydroxy compounds and their $3\alpha$-ester and ether derivatives may be prepared by opening a corresponding $2\beta,3\beta$-epoxide. In general the reaction comprises treating the corresponding $2\beta,3\beta$-epoxide with a compound $HR^3$ under acidic conditions (if necessary in the presence of an added acid catalyst, e.g. sulphuric acid, perchloric acid or boron trifluoride etherate) or a compound which produces the anion $(R^3)^-$ (where $R^3$ is as defined above), and then (when the initial product possesses a deprotonated $2\beta$-hydroxy group) treating the product with a source of protons (e.g. aqueous ammonium chloride) to form the $2\beta$-hydroxy group. Examples of $HR^3$ reagents are alcohols and carboxylic acids. Examples of reagents which produce $(R^3)^-$ anions are alkali metal or ammonium salts of $HR^3$ acids and alkali metal alkoxides. The reaction is preferably carried out under anhydrous conditions (except when $R^3 = OH$) at any suitable temperature up to reflux.

The opening of a $2\beta,3\beta$-epoxide may be carried out in a suitable solvent medium (e.g. a hydrocarbon, halogenated hydrocarbon or ether) or, when the reagent is a compound $HR^3$, an excess of the reagent may be used as the reaction solvent.

The starting materials required for the opening of a $2\beta,3\beta$-epoxide may for example be prepared by treating the corresponding $3\alpha$-bromo-$2\beta$-hydroxy compound with a base.

3. Conversion of a N,N-disubstituted $11\alpha$-amine into a N-mono-substituted compound.

Compounds of formula (I) can be prepared from corresponding $11\alpha$-tertiary amino compounds by replacement of one of the groups by a hydrogen atom, e.g. by dealkylation using for example sodium nitrite followed by catalytic hydrogenolysis.

Alternatively, the compounds may be prepared by deprotection of a corresponding 11α-(protected amino) compound having a substituent $R^1$ in addition to the protecting group, which may for example be, an acyl group such as a trichloroethoxycarbonyl, trifluoroacetyl, formyl or silyl, e.g. trimethylsilyl group. An acyl group may be removed by hydrolysis e.g. with acid or alkali. The trichloroethoxycarbonyl group may also be removed by reduction with, for example, zinc and acetic acid. Alternatively an arylmethyl protecting group such as a benzyl group may be removed by catalytic hydrogenation to produce the unprotected 11α-mono-substituted amino compound. A silyl group may be removed by e.g. solvolysis, with water (optionally containing acid or base) or an alcohol, or by treatment with a fluoride such as tetrabutylammonium fluoride.

This method may also be used to prepared compounds of formula (II) in which $R^6$ is hydrogen, by deprotection of a corresponding 11α-(protected amino) compound to yield a free 11α-amino group.

4. Esterification or transesterification of a corresponding compound having a 17β-carboxylic acid or ester group.

Compounds of formula (I) may be prepared by reacting the corresponding compound of formula (II) n which $R^7$ is hydrogen or a reactive derivative thereof (e.g. an acid halide or anhydride or a salt) with the appropriate alcohol ($R^2OH$) or alkyl or cycloalkyl halide. This reaction is preferably carried out at temperatures of $-20°$ C. to $+110°$ C., as is described for example in our British Patent Specification 1380246. Alternatively, compounds of formula (I) may be prepared by transesterification, by the reaction of a corresponding compound having a 17β-ester group with the appropriate alcohol ($R^2OH$) in the presence of an acid or base catalyst. Transesterification may be carried out at any temperature from ambient temperature to reflux, conveniently from 50° to 100° C., so as to produce a compound of formula (I) having a different 17β-ester group from the starting material; normally an excess of alcohol is used. Examples of suitable acid catalysts for transesterification include mineral acids e.g. sulphuric and hydrochloric acids, and examples of suitable base catalysts include alkali metal hydroxides and carbonates, e.g. sodium or potassium hydroxides or carbonates.

Where an alcohol is used in the esterification reaction, a coupling agent may be employed, for example a carbodiimide such as dicyclohexylcarbodiimide, preferably in the presence of a catalyst such as 4-dimethylaminopyridine.

Alternatively, esterification may be effected using a diazoalkane such as diazomethane.

Compounds of formula (II) in which $R^7$ is hydrogen can conveniently be formed by oxidising the corresponding 17β-acetyl compound, i.e. a pregnan-20-one, using for example NaOBr in an aqueous inert solvent (e.g. dioxan).

Compounds of formula (II) in which $R^7$ is a hydrogen atom may also be prepared from their corresponding esters, for example by hydrolysis under acidic or basic conditions. Examples of suitable acids for such hydrolysis include mineral acids such as hydrochloric acid; examples of suitable bases include alkali metal hydroxides and carbonates, such as sodium or potassium hydroxides or carbonates.

When using certain of the above reagents, for example alkyl halides, it may be necessary to protect the 11α-amino group, for example as a trichloroethoxycarbonyl derivative.

5. Reduction of a corresponding $\Delta^{16}$-compound.

The reduction may be effected by hydrogenation in the presence of a catalyst (e.g. a palladium catalyst) in a suitable solvent (e.g. an alcohol, ether or ester). The reaction may be effected conveniently at or about ambient temperature and atmospheric pressure in the presence of a tertiary base, e.g. triethylamine, and/or an acid, e.g. acetic acid.

The starting materials may be prepared by reaction of the corresponding 17-oxo compound with aqueous hydrogen cyanide to produce the 17-cyanohydrin which may be dehydrated to produce the $\Delta^{16}$-17β-cyano compound. This yields on hydrolysis the $\Delta^{16}$-17β-carboxylic acid and on alkylation, the corresponding $\Delta^{16}$-17β-ester.

6. Deprotection of a corresponding compound having a protected 2β or 3β group.

The 2β-hydroxy compounds of the invention may be prepared by deprotection of corresponding 2β-alkanoyloxy-3α-hydroxy or 3α-ester or -ether compounds, e.g. by hydrolysis under acidic or basic conditions. Examples of suitable acids for such hydrolysis include mineral acids such as hydrochloric acid; examples of suitable bases include alkali metal hydroxides and carbonates, such as sodium or potassium hydroxides or carbonates. This process may also result in removal of any 3α-ester or -ether or 17β-ester groups present.

The above 2β-alkanoyloxy compounds may be prepared from the corresponding 2α,3α-epoxides by reaction with the appropriate acid followed, where a 3α-ester or ether is desired, by esterification or etherification.

The 2β,3α-dihydroxy compounds according to the invention may also be prepared by deprotection of a corresponding 3α-ester or ether. The 3α-ester group may be cleaved by hydrolysis under acidic or basic conditions, e.g. using sulphuric, hydrochloric or perchloric acids or alkali metal carbonates, bicarbonates or hydroxides. The 3α-ether group may be cleaved by treatment with an aqueous acid. A cosolvent such as an alcohol, e.g. methanol may be used and the reaction may be effected at any convenient temperature up to reflux.

7. Salt formation.

Acid addition salts may be prepared by reaction of the free base with a suitable acid.

Base salts of compounds of formula (I) wherein $R^3$ contains a carboxy group or of formula (II) in which $R^7$ is hydrogen may be prepared by the reaction of the free acid with a suitable base. For example, alkali metal salts may be prepared by reaction with an alkali metal hydroxide, carbonate, bicarbonate or 2-ethylhexanoate.

The methods indicated above for preparing the compounds of the invention can be used as the last main step in a preparative sequence. The same general methods can be used for the introduction of the desired groups at an intermediate stage in the stepwise formation of the required compound, and it will be appreciated that these general methods can be combined in many different ways in such multi-stage processes. Thus for example the desired 11α-amino group may be formed either before or after the introduction of the 2β-hydroxy group. The sequence of the reactions in multi-stage processes should of course be chosen so that the reaction conditions used do not affect groups in the molecule which are desired in the final product.

The D-homo analogues of the compounds of the invention having a group —$CO_2R^2$ (or —$CO_2R^7$) at the 17aβ-position may be prepared by essentially similar methods, using appropriate starting materials of the required structure.

Various starting materials useful for the preparation of the compounds of the invention may be prepared as described in British Patent Specification No. 2080308A.

The compounds of formula (I), their D-homo analogues, and physiologically acceptable salts thereof may be formulated for administration in any convenient way, and the invention therefore includes within its scope pharmaceutical compositions comprising a compound of formula (I), a D-homo analogue thereof or a physiologically acceptable salt thereof in admixture with pharmaceutical carriers or excipients.

The compounds and their physiologically acceptable salts may for example be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, mucilage of starch or polyvinylpyrrolidone; fillers, for example lactose, sugar, maize-starch, calcium phosphate or sorbitol; lubricants, for example magnesium stearate, talc, polyethylene glycol or silica; disintegrants, for example potato starch or sodium starch glycollate; or acceptable wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The compounds of their salts may also be formulated as suppositories, e.g. containing conventional suppository bases such as cocoa butter or other glycerides.

The compounds of formula (I), their D-homo analogues, and physiologically acceptable salts thereof may also be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

When the compositions comprise dosage units, each unit will preferably contain 10–1000 mg of the active ingredient advantageously 25–500 mg. The daily dosage as employed for adult human treatment will preferably range from 25–2500 mg preferably 50–1000 mg depending on the route and frequency of administration. The compounds may be given in divided doses, for example 1–4 times per day.

The following Examples illustrate the invention.

Melting points were determined in capillaries and are corrected. Optical rotations were determined at room temperature on 1% solutions in chloroform.

Preparative t.l.c. and column chromatography were carried out on silica.

Petrol refers to petroleum ether b.p. 60°–80° C.

Solutions were dried using anhyrous sodium sulphate.

IR spectra were determined in bromoform and refer to the carbonyl stretching frequency of the 17β-carboxylic acid ester group.

INTERMEDIATE 1

Methyl 2β,3α-dihydroxy-11α-(2,2,2-trichloroethoxycarbonylamino)-5α-androstane-17β-carboxylate Methyl 2α,3α-epoxy-11α-(2,2,2-trichloroethoxycarbonylamino)-5α-androstane-17β-carboxylate (522 mg) in dioxan (5 ml) was treated with 2N sulphuric acid (1 ml) and stirred at ambient temperature for 18 h. The mixture was diluted with water (50 ml) and extracted with ethyl acetate (3×). The extract was washed with water, dried and evaporated to give a foam. This was purified by preparative t.l.c. in ethyl acetate/petrol (1:1) and crystallised from ether to give the title compound (217 mg) m.p. 228°–230°, $[\alpha]_D+27.6$.

INTERMEDIATE 2

Methyl 11α-amino-2β,3α-dihydroxy-5α-androstane-17β-carboxylate

Zinc powder (8.0 g) was added to a stirred solution of Intermediate 1 (3.9 g) in glacial acetic acid (40 ml). After 24 h the reaction mixture was diluted with chloroform (50 ml) and filtered. The filtrate was evaporated to give an oil which was diluted with water, brought to pH 10 with 0.88 NH$_3$ solution and extracted with ethyl acetate (3×). The extract was washed with water, dried and evaporated to give a foam. This was crystallised from ethyl acetate to give the title compound (1.62 g). A sample was recrystallised from ethyl acetate m.p. 166°–169°, $[\alpha]_D+53.4°$.

INTERMEDIATE 3

Methyl 2β,3β-epoxy-11α-(2,2,2-trichloroethoxycarbonylamino)-5α-androstane-17β-carboxylate Methyl 11α-(2,2,2-trichloroethoxycarbonylamino)-5α-androst-2-ene-17β-carboxylate (507 mg) in tetrahydrofuran (15 ml) and water (7.5 ml) was treated with N bromoacetamide (193 mg) and 60% perchloric acid (0.15 ml) and stirred at room temperature for 30 minutes. The reaction mixture was diluted with 5% sodium metabisulphite solution (30 ml) and water (50 ml). The suspension was extracted with ether (3×). The ether extracts were washed with water, dried and evaporated to give a foam. This was dissolved in methanol (50 ml), treated with 2M sodium hydroxide solution (10 ml), and stirred at room temperature for 30 minutes. The solution was concentrated by evaporation, diluted with water (100 ml) and extracted with ethyl acetate (3×). The extracts were washed with water (1×), dried and evaporated to give a white foam. This was purified by preparative t.l.c. in ethyl acetate/petrol (1:2) and crystallised from ether to give the title compound (90 mg) m.p. 153°–155° C., $[\alpha]_D+25.2°$.

INTERMEDIATE 4

Methyl 3α-ethoxy-2β-hydroxy-11α-(2,2,2-trichloroethoxycarbonyl-amino)-5α-androstane-17β-carboxylate Boron trifluoride diethyl etherate (0.1 ml) was added to a solution of Intermediate 3 (1.7 g) in ethanol (30 ml) and the mixture stirred at room temperature for 1 h. The mixture was concentrated by evaporation, diluted with water (100 ml) and extracted with ethyl acetate (3×). The extract was washed with water, dried and evaporated to give a froth (1.83 g). A portion was purified by preparative t.l.c. using ethyl acetate/petrol (1:1) and chloroform/methanol (9:1) to give the title compound (81 mg), $[\alpha]_D+32.9°$.

INTERMEDIATE 5

Methyl 11α-amino-3α-ethoxy-2β-hydroxy-5α-androstane-17β-carboxylate

Zinc powder (1.2 g) was added to a stirred solution of Intermediate 4 (600 mg) in glacial acetic acid (15 ml). The mixture was stirred for 17 h and the zinc was removed by filtration and was washed with acetic acid. The filtrate was evaporated and the residue diluted with dilute ammonia solution and extracted with ethyl acetate (3×). The extract was washed with water, dried and evaporated to give a froth (400 mg). A portion (100 mg) was purified by preparative t.l.c. ethyl acetate/propan-2-ol/water/ammonia (25:15:8:2) to give the title compound (56 mg), $\nu_{max}$ 1725 cm$^{-1}$.

INTERMEDIATE 6

Methyl 3α-acetoxy-2β-hydroxy-11α-(2,2,2-trichloroethoxycarbonylamino)-5α-androstane-17β-carboxylate Intermediate 3 (1.87 g) in acetic acid (30 ml) was heated on a steam bath for 75 minutes. The mixture was evaporated, the residue diluted with dilute ammonia solution and extracted with ethyl acetate (3×). The extract was washed with water (1×), dried and evaporated to give a froth (1.9 g). This was purified by preparative t.l.c. in ethyl acetate/petrol (1:1) to give a froth (800 mg). A small sample (130 mg) was purified further by preparative t.l.c. in chloroform/methanol (19:1) to give the title compound (66 mg), $[\alpha]_D+42.7°$, $\nu_{max}$ 1726 cm$^{-1}$.

INTERMEDIATE 7

Methyl 3α-acetoxy-11α-amino-2β-hydroxy-5α-androstane-17β-carboxylate

Zinc dust (1.34 g) was added to a stirred solution of Intermediate 6 (670 mg) in glacial acetic acid. After 18 h the zinc was removed by filtration and was washed with acetic acid. The filtrate was evaporated and the residue diluted with dilute ammonia solution and extracted with ethyl acetate (3×). The extract was washed with water, dried and evaporated to give a white froth (440 mg). A small sample (100 mg) was purified by preparative t.l.c. in ethyl acetate/propan-2-ol/water/ammonia (25:15:8:2) to give the title compound (55 mg), $[\alpha]_D+49.8°$.

INTERMEDIATE 8

Methyl 11α-(3-methylbutylamino)-5α-androst-2-ene-17β-carboxylate hydrosulphate

Methyl 11α-amino-androst-2-ene-17β-carboxylate (1.46 g) was dissolved in methanol (20 ml) and isovaleraldehyde (1.29 ml) was added in three portions. After stirring for 1 h at room temperature sodium borohydride (0.45 g) was added in several portions to avoid excessive gas evolution and the reaction mixture was stirred for ½ h. The methanol was removed at reduced pressure and the residual gum was partitioned between ethyl acetate and water. The layers were separated and the organic phase was washed with M—H$_2$SO$_4$, water and saturated brine, dried and concentrated to about 15 ml. Petrol was added to incipient cloudiness and the solution was allowed to crystallise to give the title compound (1.15 g), m.p. 150°–152° C.

INTERMEDIATE 9

Methyl 2β,3β-epoxy-11α-(3-methylbutylamino)-5α-androstane-17β-carboxylate

Methyl 11α-(3-methylbutylamino)-5α-androst-2-ene-17β-carboxylate (403 mg) in tetrahydrofuran (15 ml), water (7 ml) and 2M hydrochloric acid (0.5 ml) was treated with N bromoacetamide (193 mg) and 60% perchloric acid (0.15 ml) and stirred for 30 min. 5% sodium metabisulphite (30 ml) was added and the resulting solution diluted with water and brought to pH 11 with 2M sodium hydroxide solution. This was extracted with ether and the ether extracts were washed with water, dried and evaporated to give an oil. This was dissolved in methanol (50 ml), treated with 2M sodium hydroxide (10 ml) and stirred for 30 min. The solution was concentrated by evaporation, diluted with water (100 ml) and extracted with ethyl acetate (3×). The extracts were washed with water, dried and evaporated to give an oil. This was purified by preparative t.l.c. in ethyl acetate to give the title compound (185 mg), $[\alpha]_D+33.6°$.

INTERMEDIATE 10

Methyl 11α-[(N-2,2,2-trichloroethoxycarbonyl)3-methylbutylamino]-5α-androst-2-ene-17β-carboxylate Methyl 11α-(3-methylbutylamino)-5α-androst-2-ene-17β-carboxylate (1.5 g) in dichloromethane (50 ml) containing pyridine (3.0 ml) was treated with 2,2,2-trichloroethyl chloroformate (2.6 ml) and stirred for 3 h. The mixture was diluted with water (100 ml) and dichloromethane (100 ml). The dichloromethane liquors were washed with dilute hydrochloric acid, 5% sodium hydrogen carbonate solution and water, dried and evaporated to give an oil. This was purified by column chromatography, eluted with ethyl acetate/petrol (1:3), to give an oil (3.7 g). A portion (600 mg) was purified further by preparative t.l.c. in ethyl acetate/petrol (1:3) and ether/petrol (1:4) to give the title compound (255 mg), $[\alpha]_D+25.2°$.

INTERMEDIATE 11

Methyl 2α,3α-epoxy-11α-[(N-2,2,2-trichloroethoxycarbonyl)-3-methylbutylamino]-5α-androstane 17β-carboxylate Intermediate 10 (1.66 g) in dichloromethane (40 ml) was treated with m chloroperbenzoic acid (682 mg) and stirred for 2½ h. The mixture was diluted with dichloromethane (100 ml), washed with 5% sodium metabisulphite solution (2×), 5% sodium hydrogen carbonate solution (2×) and water (1×), dried and evaporated to give a foam (1.76 g). A portion (400 mg) was purified by preparative t.l.c. in ether/petrol (1:4) to give title compound (210 mg) as a froth, $[\alpha]_D+25.2°$.

INTERMEDIATE 12

2β,3α-Dihydroxy-11α-(3-methylbutylamino)-5α-androstane-17β-carboxylic acid hydrochloride Methyl 2β,3α-dihydroxy-11α-(3-methylbutylamino)-5α-androstane-17β-carboxylate (750 mg) in dioxan (20 ml) was treated with concentrated hydrochloric acid (3 ml) and water (10 ml) and heated on a steam bath for 5 days. The cooled mixture was diluted with water (200 ml) and acidified to pH 1 with dilute hydrochloric acid and extracted with ethyl acetate (3×). The extracts were washed with brine, dried and evaporated to give a foam (426 mg). This was purified by preparative t.l.c. in chloroform/methanol (4:1) to give the title compound (146 mg), $[\alpha]_D+17°$ (in dimethyl sulphoxide).

INTERMEDIATE 13

Methyl 2β,3α-dihydroxy-11α-[(N-2,2,2-trichloroethoxycarbonyl)-3-methylbutylamino]-5α-androstane-17β-carboxylate Methyl 2α,3α-epoxy-11α-[(N-2,2,2-trichloroethoxycarbonyl)-3-methylbutylamino]-5α-androstane-17β-carboxylate (1.36 g) in dioxan (15 ml) was treated with molar sulphuric acid (2.7 ml) and stirred for 6 h. The mixture was diluted with water (150 ml) and extracted with ethyl acetate (3×). The extract was washed with water, dried and evaporated to give a froth (1.28 g). A portion (400 mg) was purified by preparative t.l.c. in ethyl acetate to give the title compound (190 mg) as a froth, $[\alpha]_D+51.5°$.

EXAMPLE 1

Methyl 2β,3α-dihydroxy-11α-(3-methylbutylamino)-5α-androstane-17β-carboxylate

Intermediate 2 (1.136 g) in dimethylformamide (11 ml) was treated with 3-methylbutyliodide and heated at 65° C. for 5 h. The reaction mixture was diluted with water (100 ml) and extracted with ethyl acetate (3×). The extract was washed with water, dried and evaporated to give a solid (440 mg) which was crystallised from ether to give crystals (175 mg).

The aqueous liquors from the extraction were diluted with 0.88 NH₃ solution to pH 10 and extracted with ethyl acetate (3×). The extract was washed with water, dried and evaporated to give a foam. This was dissolved in dimethylformamide (5.5 ml), treated with 3-methylbutyliodide (0.225 ml) and potassium carbonate (216 mg) and heated at 65° C. for 5 h. The mixture was diluted with water (50 ml), brought to pH 10 by the addition of 0.88 NH₃ solution, and extracted with ethyl acetate. The extract was washed with water, dried and evaporated to give a foam. This was purified by preparative t.l.c. in methanol to give a solid. This was combined with the crystallised material (175 mg) and crystallised from ethyl acetate to give the title compound (250 mg) m.p. 163°–166°$[\alpha]_D+24.7°$.

EXAMPLE 2

Methyl 2β,3α-dihydroxy-11α-(3-methylbutylamino)-5α-androstane-17β-carboxylate

Sodium cyanoborohydride (2.0 g) and 3-methylbutanal (2.8 ml) were added to a solution of Intermediate 2 (2.0 g) in ethanol (30 ml) and the mixture stirred for 18 h. The mixture was diluted with NaHCO₃ solution and extracted with ethyl acetate (3×). The extract was washed with water (1×), dried and evaporated to give a foam. This was dissolved in ethyl acetate and extracted with dilute hydrochloric acid (3×) and water (1×). These aqueous extracts were brought to pH 10 by the addition of 0.88 NH₃ solution and then extracted with ethyl acetate (3×). This extract was washed with water, dried, filtered and evaporated to give a foam. This was purified by column chromatography eluted with chloroform/methanol (9:1) to give a foam which was crystallised from ethyl acetate to give the title compound (565 mg), m.p. 159°–161°, $[\alpha]_D+24.2°$.

EXAMPLE 3

Methyl 11α-cyclohexylamino-2β,3α-dihydroxy-5α-androstane-17β-carboxylate

Sodium cyanoborohydride (2.0 g) and cyclohexanone (2.0 ml) were added to a solution of Intermediate 2 (2.0 g) in ethanol (30 ml) and the mixture was stirred for 24 h. The mixture was diluted with NaHCO₃ solution and extracted with ethyl acetate (3×). The extract was washed with water, dried and evaporated to give a solid. This was dissolved in ethyl acetate and extracted with dilute hydrochloric acid (3×) and water (2×). These extracts were brought to pH 10 with 0.88 NH₃ solution and then extracted with ethyl acetate (3×). The ethyl acetate extract was washed with water, dried and evaporated to give a solid. This was purified by crystallisation from ethyl acetate to give the title compound (1.67 g), m.p. 199°–202°, $[\alpha]_D+6.5°$.

EXAMPLE 4

Methyl 2β,3α-dihydroxy-11α-(3-methylbutylamino)5α-androstane-17β-carboxylate hydrochloride A solution (2.34 ml; 0.0979M) of HCl in water was added to the product of Example 1 (100 mg) and the mixture stirred until a clear solution was obtained. The solution was made up to 10 g with water to give a 1% solution with pH 3.8.

EXAMPLE 5

Methyl 11α-cyclohexylamino-2β,3α-dihydroxy-5α-androstane-17β-carboxylate hydrochloride A solution (11.4 ml; 0.0979M) of HCl in water was added to the product of Example 3 (500 mg) and the mixture stirred until a clear solution was obtained. The solution was made up to 25 g with water to give a 2% solution with pH 2.7.

EXAMPLE 6

Methyl 3α-ethoxy-2β-hydroxy-11α-(3-methylbutylamino)-5α-androstane-17β-carboxylate Sodium cyanoborohydride (27 mg) was added to a mixture of Intermediate 5 (300 mg). After 1 h sodium borohydride (50 mg) was added and the mixture stirred for a further 2 h. Water (150 ml) was added and the suspension extracted with ethyl acetate (3×). These extracts were washed with brine (2×), dried and evaporated to give a froth (346 mg). This was purified by preparative t.l.c. in chloroform/methanol (9:1) to give the title compound (166 mg), $[\alpha]_D + 30.6°$, $\nu_{max}$ 1725 cm$^{-1}$.

EXAMPLE 7

Methyl 2β,3α-dihydroxy-11α-(3-methylbutylamino)-5α-androstane-17β-carboxylate Methyl 3α-acetoxy-2β-hydroxy-11α-(3-methylbutylamino)-5α-androstane-17β-carboxylate (20 mg) in ethanol (5 ml) was treated with 2M sodium hydroxide and stirred at room temperature for 18 h. The mixture was evaporated to dryness and the residue dissolved in ethyl acetate The ethyl acetate liquors were washed with water, dried, and evaporated to give a white solid (8 mg). T.l.c. in ethyl acetate/0.88 ammonia (50:1) showed a spot ($R_f$ 0.36) compatible with the title compound.

EXAMPLE 8

Methyl 2β,3α-dihydroxy-11α-(3-methylbutylamino)-5α-androstane-17β-carboxylate Intermediate 9 (450 mg) in dioxan (5 ml) was treated with 1M sulphuric acid (1 ml) and stirred for 4 h. The mixture was concentrated by evaporation, diluted with 0.88 ammonia solution and extracted with ethyl acetate (3×). The extracts were washed with water, dried and evaporated to give an oil. This was purified by preparative t.l.c. in ethyl acetate/0.88 ammonia (50:1) to give the title compound (85 mg) as a solid, $[\alpha]_D + 22.4°$.

EXAMPLE 9

Propyl 2β,3α-dihydroxy-11α-(3-methylbutylamino)-5α-androstane-17β-carboxylate A solution of methyl 2β,3α-dihydroxy-11α-(3-methylbutylamino)-5α-androstane-17β-carboxylate (437 mg) in propan-1-ol (30 ml) was heated at 100° C. with conc. sulphuric acid (0.2 ml) for 40 h. The cooled mixture was concentrated by evaporation and the residue diluted with water (150 ml) and brought to pH 10 by the addition of 0.88 ammonia solution. The suspension was extracted with ethyl acetate (3×) and the extracts washed with brine, dried and evaporated to give a solid. This was crystallised from ethyl acetate to give the title compound (70 mg), m.p. 140°–142° C., $[\alpha]_D + 17.2°$.

EXAMPLE 10

Methyl 2β,3α-dihydroxy-11α-(3-methylbutylamino)-5α-androstane-17β-carboxylate A solution of propyl 2β,3α-dihydroxy-11α-(3-methylbutylamino)-5α-androstane-17β-carboxylate (100 mg) in methanol (10 ml) was heated at 100° C. with concentrated sulphuric acid (0.2 ml) for 48 h. The cooled mixture was evaporated, the residue brought to pH 10 by the addition of 0.88 ammonia solution and extracted with ethyl acetate (3×). The extracts were washed with water, dried and evaporated to give the title compound (80 mg), $[\alpha]_D + 22.4°$.

EXAMPLE 11

Cyclohexyl 2β,3α-dihydroxy-11α-(3-methylbutylamino)-5α-androstane-17β-carboxylate Methyl 2β,3α-dihydroxy-11α-(3-methylbutylamino)-5α-androstane-17β-carboxylate (410 mg) in cyclohexanol (2.5 ml) was heated at 100° C. with concentrated $H_2SO_4$ (0.2 ml) for 24 h. The cooled mixture was concentrated by evaporation and the residue purified by column chromatography using ethyl acetate/ammonia 50:1 to give an oil (194 mg). This was purified further by preparative t.l.c. in ethyl acetate/ammonia 50:1 to give the title compound (40 mg), $[\alpha]_D + 17°$, $\nu_{max}$ 1725 cm$^{-1}$.

EXAMPLE 12

Methyl 2β,3α-dihydroxy-11α-(3-methylbutylamino)-5α-androstane-17β-carboxylate Intermediate 8 (0.5 g) was dissolved in glacial acetic acid (0.6 ml) and the solution was diluted with M-$H_2SO_4$ (0.5 ml). A solution of peracetic acid in glacial acetic acid (0.2 ml, 40% w/v) was then added and the mixture was allowed to stand overnight. Sodium sulphite solution (2 ml, 10% w/v) was added followed after 10 min. by methylene chloride (20 ml). The pH of the mixture was raised from 3 to 5 with 5M-NaOH and the layers were separated. The aqueous phase was extracted with methylene chloride (2×) and the combined extracts were azeotropically dried and evaporated to an oil (0.708 g). The oil was dissolved in methanol (10 ml), concentrated $H_2SO_4$ (0.2 ml) was added and the solution was heated at reflux for 20 h. The cooled solution was diluted with water (10 ml) and washed with methylene chloride (2×). The separated aqueous layer was basified to pH 11 with 5M-NaOH in the presence of methylene chloride (10 ml) and further extracted with methylene chloride (2×). The combined extracts were washed with water, azeotropically dried and evaporated to a foam (0.156 g,). A further quantity of crude product was obtained from the original, acidic methylene chloride extract by water addition, pH adjustment, extraction and evaporation (0.273 g). The combined crude products were crystallised from ethyl acetate to give the title compound (0.219 g), m.p. 157°–160° C.

EXAMPLE 13

Methyl 3α-acetoxy-2β-hydroxy-11α-(3-methylbutylamino)-5α-androstane-17β-carboxylate Sodium cyanoborohydride (30 mg) was added to a stirred solution of Intermediate 7 (340 mg) in ethanol (15 ml). After 2 h sodium borohydride (50 mg) was added and the mixture stirred for a further 2 h. Water (200 ml) was added and the suspension extracted with ethyl acetate (3×). The extract was washed with brine (2×), dried and evaporated to give a froth (394 mg). This was purified by preparative t.l.c. in chloroform/methanol (9:1) to give the title compound (196 mg), $[\alpha]_D+32.2°$, $\nu_{max}1725$ cm$^{-1}$.

EXAMPLE 14

Methyl 2β,3α-dihydroxy-11α-(3-methylbutylamino)-5α-androstane-17β-carboxylate Methyl 2β,3α-dihydroxy-11α-[(N-2,2,2-trichloroethoxycarbonyl)-3-methylbutylamino]-5α-androstane-17β-carboxylate (875 mg) in glacial acetic acid (30 ml) was treated with zinc powder (1.75 g) and stirred for 19 h. The zinc was removed by filtration and washed with acetic acid. The filtrate was evaporated and the residue diluted with dilute ammonia solution and extracted with ethyl acetate (3×). The extract was washed with water, dried and evaporated to give a froth (538 mg). This was purified by preparative t.l.c. in ethyl acetate/0.88 ammonia (50:1) to give the title compound (185 mg) as a froth, $[\alpha]_D+23.7°$.

EXAMPLE 15

Methyl 3α-ethoxy-2β-hydroxy-11α-(3-methylbutylamino)-5α-androstane-17β-carboxylate hydrochloride solution Methyl 3α-ethoxy-2β-hydroxy-11α-(3-methylbutylamino)-5α-androstane-17β carboxylate (100 mg) was dissolved in 0.0987M HCl solution (2.2 ml) as far as possible. The mixture was made up to 15 g the addition of water and filtered. The residue was collected, dried and weighed. This gave a 0.56% solution with respect to free base, pH 2.2.

EXAMPLE 16

Methyl 3α-acetoxy-2β-hydroxy-11α-(3-methylbutylamino)-5α-androstane-17β-carboxylate hydrochloride solution Methyl 3α-acetoxy-2β-hydroxy-11α-(3-methylbutylamino)-5α-androstane-17β-carboxylate (90 mg) was dissolved in 0.0987M HCl solution (1.91 ml) as far as possible. The mixture was made up to 9 g with water and filtered. The residue was collected, dried and weighed (9 mg). This gave a 0.9% solution with respect to free base, pH 2.45.

EXAMPLE 17

Propyl 2β,3α-dihydroxy-11α-(3-methylbutylamino)-5α-androstane-17β-carboxylate hydrochloride solution Propyl 2β,3α-dihydroxy-11α-(3-methylbutylamino)-5α-androstane-17β-carboxylate (40 mg) was dissolved in 0.0987M HCl solution (0.88 ml), made up to 8 g with water and filtered. This gave a 0.5% solution with respect to free base, pH 3.8.

EXAMPLE 18

2β,3α-Dihydroxy-11α-(3-methylbutylamino)-5α-androstane-17β-carboxylic acid hydrochloride solution 2β,3α-Dihydroxy-11α-(3-methylbutylamino)-5α-androstane-17β-carboxylic acid hydrochloride (70 mg) was dissolved in water (7 ml) to give a 1% solution with respect to the hydrochloride salt, pH 4.1.

EXAMPLE 19

Methyl 11α-(3,3-dimethylbutylamino)-2β,3α-dihydroxy-5α-androstane-17β-carboxylate Sodium cyanoborohydride (1.5 g) was added to a mixture of methyl 11α-amino-2β,3α-dihydroxy-5α-androstane-17β-carboxylate (760 mg) and 3,3-dimethylbutyraldehyde (700 mg) in ethanol (30 ml). The mixture was stirred for 18 h, diluted with 5% sodium hydrogen carbonate solution and extracted with ethyl acetate (3×). The extract was washed with water, dried and evaporated to give a foam (1.18 g) which was purified by preparation t.l.c. in ethyl acetate/0.88 ammonia (50:1) to give the title compound (565 mg) as a foam, $[\alpha]_D+22.1°$, $\nu_{max}$ 1725 cm$^{-1}$.

The following examples illustrate pharmaceutical formulations of the compounds according to the invention:

EXAMPLE A

TABLE

| Wet granulated | mg/tablet |
| --- | --- |
| Methyl 2β,3α-hydroxy-11α-(3-methylbutylamino)-5α-androstane-17β-carboxylate hydrochloride | 108.00 |
| Maize starch | 138.0 |
| Polyvinyl pyrrolidone | 2.5 |
| Sodium starch glycolate | 7.5 |
| Magnesium stearate | 2.0 |
| Tablet weight | 258.00 |

Sieve the steroid and maize starch through a 40 mesh screen. Blend the maize starch with the steroid in a suitable blender. Make a 5–10% w/v aqueous solution of the polyvinyl pyrrolidone. Add this solution to the mixing powder and mix until granulated. Pass the granulate through a number 12 screen. Dry the granules at 50° C. in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine.

The tablets may be coated with a thin polymeric coat applied by the usual techniques. The film coat may contain a pigment.

EXAMPLE B

TABLE

| Direct compression | mg/tablet |
| --- | --- |
| Methyl 2β,3α-dihydroxy-11α-(3-methylbutylamino)-5α-androstane-17β-carboxylate hydrochloride | 108.00 |
| Microcrystalline cellulose | 134.00 |
| Starch 1500 | 100.00 |
| Sodium starch glycolate | 6.00 |
| Magnesium stearate | 2.00 |
| Tablet weight | 350.00 |

Sieve the active ingredient and microcrystalline cellulose and starch 1500 through a 40 mesh sieve. Sieve the sodium starch glycolate and magnesium stearate through a 60 mesh sieve. Blend the powders together in a suitable blender until homogeneous. Compress with appropriate punches on an automatic tablet press. The tablets may be covered by a thin polymer coat applied by the usual film coating techniques. A pigment may be included in the film coat.

EXAMPLE C

| Hard gelatin capsule | mg/capsule |
|---|---|
| Methyl 2β,3α-dihydroxy-11α-(3-methylbutylamino)-5α-androstane-17β-carboxylate hydrochloride | 54.0 |
| Lactose, anhydrous | 141.0 |
| Sodium starch glycolate | 4.0 |
| Magnesium stearate | 1.0 |
| Capsule fill weight | 200.0 mg |

The steroid is sieved and blended by a gradual dilution technique with the sieved excipients, in a suitable blender. The blend is then filled into suitable size hard gelatin capsule shells using an automatic machine.

EXAMPLE D

| Intravenous Injection | % w/v |
|---|---|
| Methyl 2β,3α-dihydroxy-11α-(3-methylbutylamino)-5α-androstane-17β-carboxylate hydrochloride | 0.1-1.0 |
| Sodium metabisulphite | 0.1 |
| Sodium citrate BP | 0.1 |
| Citric acid monohydrate BP | 0.1 |
| Sodium chloride | 0.7 |
| Water for Injections to | 100 |

METHOD OF MANUFACTURE

Dissolve the steroid in approximately half the total volume of Water for Injections. Add the sodium metabisulphite, sodium citrate, sodium chloride and citric acid and stir to dissolve. Make the solution up to the final volume using more Water for Injections. Filter the solution throught a 0.22μ membrane and fill aseptically into the final sterilized containers.

We claim:

1. Compounds of the formula

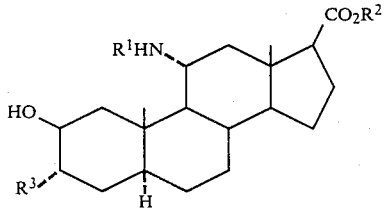

(I)

wherein $R^1$ is a $C_{1-8}$ alkyl group or a $C_{3-7}$ cycloalkyl group;
$R^2$ is a $C_{1-6}$ alkyl group or a $C_{3-7}$ cycloalkyl group;
$R^3$ is a hydroxy group or a group of formula —$OR^4$ or —$OCOR^5$ where
$R^4$ is an alkyl or alkenyl group which may contain up to 6 carbon atoms (or such a group substituted by halogen, $C_{1-6}$ alkoxy, carboxy, phenyl, phenyl substituted by nitro, halo, $C_{1-4}$ alkoxy or $C_{1-4}$ alkyl), a $C_{3-7}$ cycloalkyl group, a phenyl group (or such a group substituted by nitro, halo, $C_{1-4}$ alkoxy or $C_{1-4}$ alkyl), or a carbon-attached 5–7 membered heterocyclic ring in which the hetero atom is selected from nitrogen, oxygen and sulphur, and
$R^5$ is a hydrogen atom or a group $R^4$ as defined above;
and the D-homo analogues thereof having the group —$CO_2R^2$ (wherein $R^2$ is as defined above) at the 17aβ-position, and salts thereof.

2. Compounds as claimed in claim 1 wherein $R^1$ is an isopentyl, hexyl, isohexyl, neohexyl, cyclopentyl or cyclohexyl group.

3. Compounds as claimed in claim 1 wherein $R^2$ is a methyl or ethyl group.

4. Compounds as claimed in claim 1 wherein $R^3$ is a hydroxy group.

5. Compounds as claimed in claim 1 in the form of physiologically acceptable acid addition salts.

6. Compounds as claimed in claim 5 in the form of hydrochloride, hydrobromide, phosphate, sulphate, p-toluenesulphonate, methanesulphonate, citrate, tartrate, acetate, ascorbate, lactate, maleate, succinate, tricarballylate, glutarate and glutaconate acid addition salts.

7. Compounds of formula (I) as claimed in claim 1 selected from:
 (a) methyl 2β,3α-dihydroxy-11α-(3-methylbutylamino)-5αp-androstane-17β-carboxylate;
 (b) methyl 11α-cyclohexylamino-2β,3α-dihydroxy-5α-androstane-17β-carboxylate;
 (c) methyl 3α-ethoxy-2β-hydroxy-11α-(3-methylbutylamino)-5α-androstane-17β-carboxylate; and
 (d) methyl 3α-acetoxy-2β-hydroxy-11α-(3-methylbutylamino)-5α-androstane-17β-carboxylate;
and their physiologically acceptable acid addition salts.

8. Pharmaceutical compositions comprising at least one compound of formula (I) or D-homo analogue thereof as claimed in claim 1 or a physiologically acceptable salt thereof in admixture with one or more pharmaceutical carriers or excipients.

9. Compounds of the formula

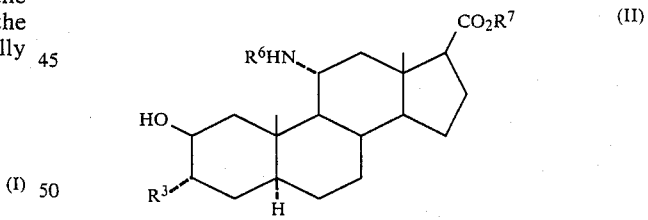

(II)

(wherein $R^6$ is a hydrogen atom, a $C_{1-8}$ alkyl group or a $C_{3-7}$ cycloalkyl group; $R^7$ is a hydrogen atom, a $C_{1-6}$ alkyl group or a $C_{3-7}$ cycloalkyl group; and $R^3$ is as defined in claim 1; with the proviso that at least one of $R^6$ and $R^7$ is a hydrogen atom) and the D-homo analogues thereof having the group —$CO_2R^7$ (wherein $R^7$ is as defined above) in the 17aβ-position and salts thereof.

10. A method of therapy or prophylaxis of a human or animal body suffering from or liable to cardiac dysrhythmias which method comprises administering to the said body an effective amount of a compound of formula (I), a D-homo analogue thereof, or physiologically acceptable salt thereof as claimed in claim 1.

11. Compounds of formula (I), D-homo analogues thereof, and physiologically acceptable salts thereof as claimed in claim 1 for use in a method of treatment of the human or animal body to combat cardiac dysrhythmias therein.

12. Compounds as claimed in claim 2 wherein $R^2$ is a methyl or ethyl group.

13. Compounds as claimed in claim 2 wherein $R^3$ is a hydroxy group.

14. Compounds as claimed in claim 3 wherein $R^3$ is a hydroxy group.

15. Compounds as claimed in claim 2 wherein $R^2$ is a methyl or ethyl group and $R^3$ is a hydroxy group.

16. Compounds as claimed in claim 2 in the form of physiologically acceptable acid addition salts.

17. Compounds as claimed in claim 3 in the form of physiologically acceptable acid addition salts.

18. Compounds as claimed in claim 4 in the form of physiologically acceptable acid addition salts.

* * * * *